United States Patent
Richard et al.

[11] Patent Number: 6,080,880
[45] Date of Patent: Jun. 27, 2000

[54] SILICONE-SUBSTITUTED CINNAMAMIDE/ MALONAMIDE/MALONATE COMPOUNDS AND PHOTOPROTECTIVE COMPOSITIONS COMPRISED THEREOF

[75] Inventors: Hervé Richard, Villepinte; Madeleine Leduc, Paris, both of France

[73] Assignee: Societe L'Oreal S.A., Paris, France

[21] Appl. No.: 08/980,307

[22] Filed: Nov. 28, 1997

[51] Int. Cl.[7] .................................. C07F 7/08; C07F 7/10
[52] U.S. Cl. ........................ 556/419; 556/440; 514/63; 424/60; 424/70.2; 424/70.9; 424/401
[58] Field of Search ..................... 556/419, 440; 514/63; 424/406, 70.9, 70.2, 60

[56] References Cited

U.S. PATENT DOCUMENTS

| | | |
|---|---|---|
| 4,876,084 | 10/1989 | Hori et al. |
| 5,093,511 | 3/1992 | Yoshida et al. |
| 5,315,022 | 5/1994 | Yoshida et al. |
| 5,908,949 | 6/1999 | O'Lenick et al. ............. 556/440 |
| 5,976,558 | 6/1999 | Richard et al. ............... 424/60 |

FOREIGN PATENT DOCUMENTS

| | | |
|---|---|---|
| 0 138 590 A2 | 4/1985 | European Pat. Off. |
| 0138321 | 4/1985 | European Pat. Off. |
| 0138590 | 4/1985 | European Pat. Off. |
| 0157481 | 10/1985 | European Pat. Off. |
| 60-108431 | 6/1985 | Japan |
| 63-39847 | 2/1988 | Japan |
| 2-117613 | 5/1990 | Japan |
| 6-501490 | 2/1994 | Japan |
| 9-221407 | 8/1997 | Japan |
| WO 92/19223 | 11/1992 | WIPO |
| 93/10745 | 6/1993 | WIPO |

OTHER PUBLICATIONS

Chemical Abstracts, vol. 126, No. 3, Jan. 20, 1997, Columbus Ohio; abstract No. 36860.
Chemical Abstracts, vol. 116, No. 19, May, 11, 1992, Columbus Ohio; abstract No. 194586c.
Chemical Abstracts, vol. 117, No. 5, Aug. 3, 1992, Columbus, Ohio; abstract No. 48900e.
Chemical Abstracts, vol. 123, No. 26, Dec. 25, 1995, Columbus Ohio; abstract No. 349880q.
Chemical Abstracts, vol. 115, No. 16, Oct. 21, 1991, Columbus, Ohio; abstract No. 160540x.

*Primary Examiner*—Paul F. Shaver
*Attorney, Agent, or Firm*—Burns, Doane, Swecker & Mathis, L.L.P.

[57] ABSTRACT

Novel silicone-substituted cinnamamide/malonamide/ malonate compounds having the structural formulae (1) and (2):

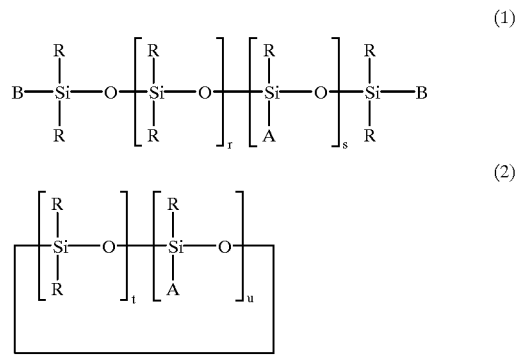

in which A is a radical of formula (3):

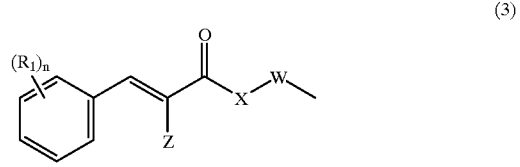

are well suited for the photoprotection of human skin and/or hair against the damaging effects of UV-A and UV-B irradiation, particularly solar radiation, and are also useful for photoprotecting such UV-sensitive substrates as plastics.

20 Claims, No Drawings

SILICONE-SUBSTITUTED CINNAMAMIDE/ MALONAMIDE/MALONATE COMPOUNDS AND PHOTOPROTECTIVE COMPOSITIONS COMPRISED THEREOF

CROSS-REFERENCE TO COMPANION APPLICATION

Our copending application Serial No. 08/969,365 Nov. 28, 1997 filed concurrently herewith and assigned to the assignee hereof.

BACKGROUND OF THE INVENTION

1. Technical Field of the Invention

The present invention relates to novel cinnamamide, benzalmalonamide and benzalmalonate compounds bearing short-chain silicone substituents on the aromatic moieties thereof.

This invention also relates to compositions of matter, in particular cosmetic compositions, comprising the above novel compounds, which are especially well suited for the photoprotection of the skin and/or the hair against the deleterious effects of UV radiation, in particular solar radiation.

2. Description of the Prior Art

It is known to this art that light radiation of wavelengths of from 280 nm to 400 nm promotes tanning of the human epidermis, and that light radiation of wavelengths more particularly of from 280 to 320 nm, i.e., UV-B irradiation, causes skin burning and erythema which can impair the development of a natural tan. For these reasons, as well as for aesthetic reasons, there is an increasing demand for means of controlling this natural tanning in order to thereby control the color of the skin. This UV-B radiation must thus be screened from the skin.

It is also known to this art that UV-A radiation, of wavelengths of from 320 to 400 nm, which tan the skin, also adversely affects it, especially in the case of sensitive skin or skin which is continually exposed to solar radiation. UV-A rays especially cause a loss in the elasticity of the skin and the appearance of wrinkles, promoting premature skin aging. Such irradiation promotes triggering of the erythemal reaction or amplifies this reaction in certain individuals and may even be the source of phototoxic or photoallergic reactions. Thus, for aesthetic and cosmetic reasons, such as conservation of the natural elasticity of the skin, for example, an ever-increasing number of individuals wish to control the effect of UV-A rays on their skin, it is desirable to also screen out UV-A radiation.

A wide variety of compounds suited for photoprotection (UV-A and/or UV-B) of the skin are known to this art.

Most of these are aromatic compounds exhibiting absorption of UV radiation in the region from 280 to 315 nm, or in the region from 315 to 400 nm, or in both of these regions. They are typically formulated into antisun or sunscreen compositions which are in the form of an emulsion of oil-in-water type (namely, a cosmetically acceptable vehicle, diluent or carrier comprising a dispersing continuous aqueous phase and a dispersed discontinuous oily phase) and which thus contain, in various concentrations, one or more conventional lipophilic and/or hydrophilic organic screening agents including an aromatic function. These are capable of selectively absorbing harmful UV radiation, such screening agents (and their amounts) being selected as a function of the desired sun protection factor SPF (the sun protection factor being expressed mathematically by the ratio of the irradiation time required to attain the erythema-forming threshold with the UV screening agent to the time required to attain the erythema-forming threshold in the absence of UV screening agent).

Other than their screening power, these compounds exhibiting anti-UV activity must also have good cosmetic properties in compositions comprised thereof, good solubility in the usual solvents, and in particular fatty substances such as oils and greases, as well as good resistance to water and to perspiration (remanence).

Among all of the aromatic compounds which are suited for this purpose, particularly well suited are the silicon-containing benzalmalonate compounds described in EP-A-358,584 and in EP-A-392,882, both assigned to the assignee hereof. Admittedly, these compounds have good liposolubility. However, they also comprise very long silicone chains and, taking account of their bulk, their synthesis, as well as their formulation into cosmetic compositions, is not without difficulty. Lastly, their cosmetic properties are not always satisfactory.

SUMMARY OF THE INVENTION

A major object of the present invention is the provision of novel cinnamamide, benzalmalonamide and benzalmalonate compounds bearing short-chain silicone substituents on the aromatic moieties thereof, these novel compounds having, besides very good solubility in fatty materials, improved cosmetic properties, and which otherwise avoid those disadvantages and drawbacks to date characterizing the state of this art.

Even more specifically, it has now been found that by grafting at least one cinnamamide, benzalmalonamide or benzalmalonate group onto a short-chain silicone molecule, in particular onto a linear silicone chain comprising not more than six Si atoms, novel compounds are obtained which obviate the drawbacks of the screening agents of the prior art, these novel compounds having, other than very high-performance screening properties, very good solubility in the usual organic solvents and in particular fatty substances such as oils, as well as excellent cosmetic properties, which render them particularly suitable for use as sunscreens in, or for the formulation of, cosmetic compositions suited for protecting the skin and/or the hair against the deleterious effects of ultraviolet radiation. And, taking account of their relatively small size, these novel compounds are easier to synthesize.

Thus, the present invention features novel compounds having one of the formulae (1) or (2) below:

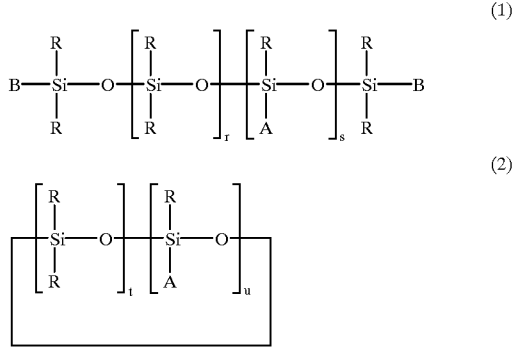

in which the radicals R, which may be identical or different, are each a saturated or unsaturated, linear or branched $C_1$–$C_{10}$ alkyl radical, a phenyl radical or a 3,3,3-trifluoropropyl radical, at least 80% by number of the radicals R being methyl radicals; the radicals B, which may be identical or different, are each a radical R or a radical A; r is an integer ranging from 0 to 3, inclusive; s is 0 or 1 and if s is 0, at least one of the two radicals B is A; u is equal to 1 or 2; t is an integer ranging from 2 to 5 inclusive; t+u is greater than or equal to 3; and A is a radical of formula (3) below:

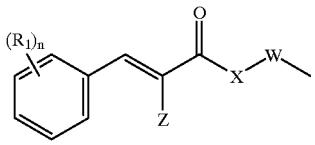

(3)

wherein $R_1$ is a linear or branched $C_1$–$C_{10}$ alkoxy radical, a linear or branched $C_1$–$C_{10}$ alkyl radical, a linear or branched $C_2$–$C_8$ alkenyl radical or a radical —OSi(CH$_3$)$_3$, with the proviso that two adjacent radicals $R_1$ may together form an alkylidenedioxy radical in which the alkylidene radical has from 1 to 2 carbon atoms, n is 0, 1, 2 or 3, Z is hydrogen, a $C_1$–$C_4$ alkyl radical, a radical —(C=O)X$R_2$ or a radical —(C=O)YW, X and Y, which may be identical or different, are each an oxygen atom or a radical —N$R_3$, W is a saturated or unsaturated, linear or branched $C_1$–$C_6$ alkanediyl radical, optionally substituted with a hydroxyl or saturated or unsaturated, linear or branched $C_2$–$C_8$ alkyl radical, $R_2$ is, independently, a $C_1$–$C_{12}$ alkyl radical, $R_3$ is, independently, hydrogen or a linear or branched $C_1$–$C_8$ alkyl radical, with the proviso that $R_2$ and $R_3$ may together form a heterocycle, with the added proviso that when Z=H, then X is the radical —N$R_3$—.

DETAILED DESCRIPTION OF BEST MODE AND SPECIFIC/PREFERRED EMBODIMENTS OF THE INVENTION

More particularly according to the present invention, by the term "heterocycle" is preferably intended a piperidino, morpholino, pyrrolidino or piperazino radical, optionally substituted in the 4-position with a $C_1$–$C_6$ alkyl radical.

The compounds of the invention differ from those of EP-A-392,882 in that the silicone chain(s) grafted onto the aromatic moieties of the cinnamamide, benzalmalonamide or benzalmalonate basic nuclei have not more than six Si atoms when they are linear and not more than seven Si atoms when they are cyclic. Although, in this fashion, these compounds comprise a short-chain silicone, they have excellent liposolubility and can thus be used in large concentrations, which imparts to the final compositions very high protection factors. Moreover, they are distributed uniformly in conventional cosmetic media containing at least one fatty phase or a cosmetically acceptable organic solvent and can thus be topically applied to the hair or the skin to provide an effective protective film. Furthermore, their cosmetic properties are very good, i.e., in particular, these products are less sticky and provide more softness than the screening silicones of the prior art.

In addition, the compounds of the invention have an excellent intrinsic screening power with regard to UV-A and UV-B ultraviolet radiation.

These novel silicone-substituted cinnamamide, benzalmalonamide and benzalmalonate compounds are thus useful sunscreens for human skin and hair. They are also useful photoprotective agents for plastics.

The cinnamamide, benzalmalonate or benzalmalonamide compounds of formula (1) or (2) advantageously have at least one of the following characteristics:

R is methyl,

B is methyl, r is 0 or 1, s is 1, t+u ranges from 3 to 5, n is 0 or 1, $R_1$ is methoxy, $R_2$ is methyl or ethyl, $R_3$ is H.

Preferably, the compounds according to the present invention are compounds of formula (1) or (2) having all of the following characteristics:

R is methyl,

B is methyl, r=0, s=1, $R_1$ is methoxy.

To prepare the compounds of formula (1) or (2), a synthesis can be employed (route A) by carrying out a hydrosilylation reaction starting with the corresponding siloxane derivative in which, for example, all the radicals A are hydrogen atoms. This derivative is referred to hereinbelow as the SiH derivative.

The SiH groups can be present along the chain and/or at the ends of the chain. These SiH derivatives are compounds that are well known to the silicone arts and are generally commercially available. They are described, for example, in U.S. Pat. Nos. 3,220,972, 3,697,473 and 4,340,709.

The SiH compounds corresponding to those of formulae (1) and (2) can thus be represented by formulae (4) and (5) below:

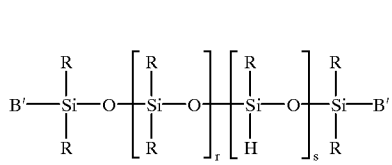

(4)

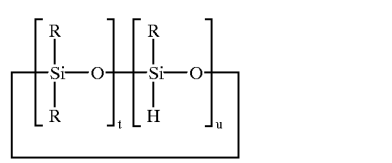

(5)

in which R, r, s, t and u are as defined above in formulae (1) and (2); and the radicals B', which may be identical or different, are each a radical R or a hydrogen atom.

A hydrosilylation reaction is carried out of this SiH derivative of formula (4) or (5) in the presence of a catalytically effective amount of a platinum catalyst, on an organic compound selected from among those of formula (6) below:

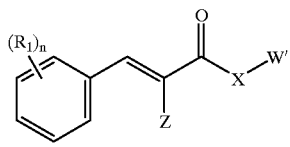

(6)

in which $R_1$, X, Z and n are as defined in formula (3) above and in which W' has the same definition as W in formula (3) above, but is terminated either with a double bond or with a triple bond.

The hydrosilylation reaction is thus carried out according to one of the following two reaction mechanisms:

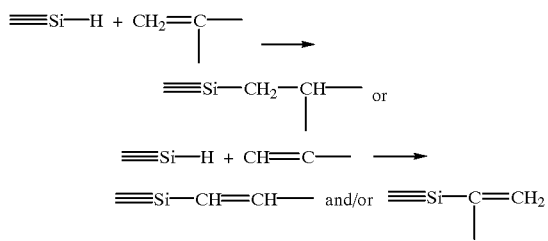

The compounds of formula (6) are thus the following compounds:

(1) benzalmalonate compounds having the following formula:

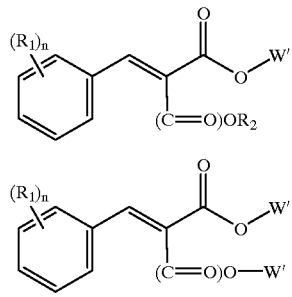

in which $R_1$, $R_2$, W' and n are as defined in formula (6) above, (2) benzalmalonamide compounds having the following formulae:

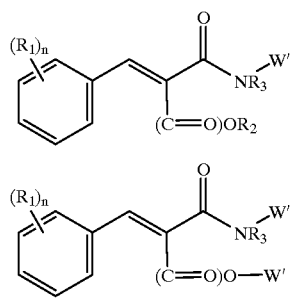

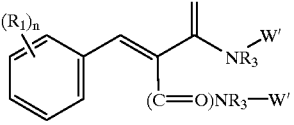

in which $R_1$, $R_2$, $R_3$, W' and n are as defined in formula (6) above, (3) cinnamamide compounds having the following formula:

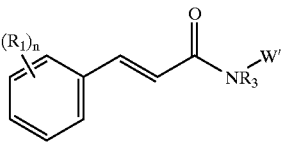

in which $R_1$, $R_3$, W' and n are as defined in formula (6) above.

Thus, benzalmalonate derivatives which are particularly suitable for the preparation of compounds according to the invention include diallyl 4-methoxybenzylidenemalonate, described in FR-2,483,401, and diallyl benzylidenemalonate, described in Liebigs *Ann. Chem.*, 1483 (1978).

Exemplary cinnamamide compounds which are particularly suitable for the preparation of the compounds according to the invention, include N-allyl-3,4-dimethoxycinnamamide, described in *J. Med. Chem.*, 7, 319 (1964) and in JP-04,134,028, N-allyl-3,4,5-trimethoxycinnamamide, described in U.S. Pat. No. 3,268,407, and N-allyl-3-methoxy-4-octyloxycinnamamide, described in *Acta Pharm. Hung.*, 39, 66 (1969).

Another route (route B) for the synthesis of the compounds of formulae (1) and (2) entails carrying out a hydrosilylation reaction on the SiH derivatives of formula (4) or (5) in the presence of a catalytically effective amount of a platinum catalyst, on an organic compound having the formula (7) below:

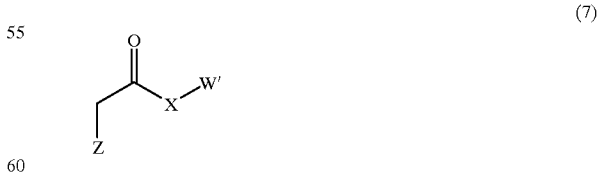

in which Z, X and W' are as defined in formula (6) above.

The silicone derivative thus obtained, of formula (7') or (7") below:

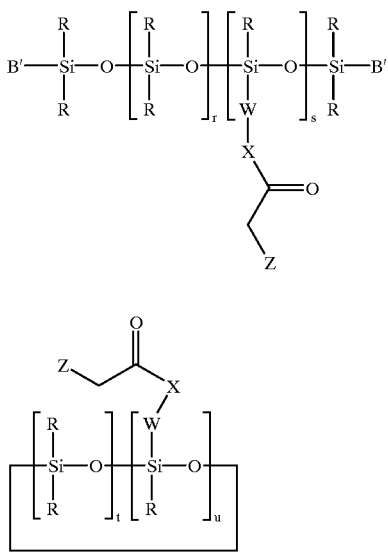

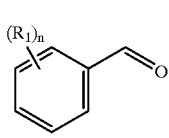

is then reacted with a benzaldehyde of formula (8) below:

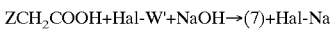

in which formulae (7), (7') and (8) X, W', Z, R$_1$ and n are as defined above.

The compounds of formula (7) in the event that X=O are prepared by alkylation of the corresponding acid with a halide of an unsaturated derivative (Hal) in the presence of a base, according to the following reaction scheme:

ZCH$_2$COOH+Hal-W'+NaOH→(7)+Hal-Na

The compounds of formula (7) in the event that X=NR$_3$ are prepared by reaction of the corresponding acid chloride with an unsaturated amine according to the following reaction scheme:

ZCH$_2$COCl+HNR$_3$—W'→(7)+HCl

Another route (route C) for the preparation of the compounds of formulae (1) and (2) in which X is the —NH— radical entails first reacting the derivative of formula (9) below:

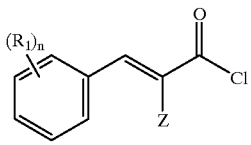

with an aminosiloxane of formula (10) or (11) below:

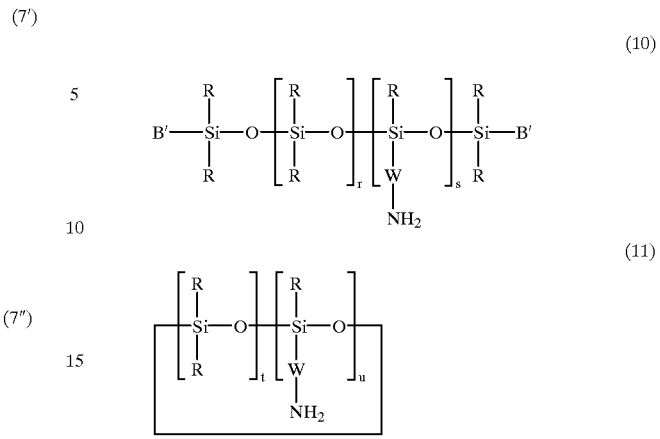

in which R, r, s, t and u are as defined in formulae (1) and (2), and the radicals B', which may be identical or different, are each a radical R or an —NH$_2$ radical.

The preparation of the compounds of formula (9), such as 4-methoxycinnamyl chloride, is described in particular in *Farmacia*, 9, pages 345–350 (1961).

The preparation of the aminosiloxanes is described, for example, in GB 2,185,984. Exemplary aminosiloxanes which are particularly suitable for the preparation of the compounds according to the invention include aminopropylhepta-methyltrisiloxane, aminoisobutylheptamethyltrisiloxane and trimethylsilylamodimethicones, such as the product marketed under the trademark "X$_2$-8260" by Dow Corning, having an amine index of 2.8 meq/gram; the product marketed under the trademark "SLM 55051/3" by Wacker, having an amine index of 0.47 meq/gram; C$_{12}$ dimethylalkyl PDMSs, such as the product marketed under the trademark "SLM 23046/1" by Wacker, having an amine index of 1.2 meq/gram; α, ω-trimethylated polymethylalkyl (fatty) arylalkylsiloxanes, such as the product marketed under the trademark "SLM 23056/2" by Wacker, having an amine index of 1.3 meq/gram; PDMSs whose NH$_2$ radical is in position α and ω on an alkyl site, such as the products marketed under the trademarks "Tegomer A-SI 2120", having an amine index of 1.95 meq/gram and "Tegomer A-SI 2320" with an amine index of 0.86 meq/gram, marketed by Goldschmidt.

The preparation of the cyclic aminosiloxanes is described, for example, in the article by A. Kopylov, *Zh. Obshch. Khim.*, 54 (2), 367–71 (1984).

The present invention also features compositions comprising a compound of formula (1) or (2) formulated into a suitable support or medium therefor. The support can be, for example, a plastic. It can also be suitable for topical application. In this instance, the composition according to the invention is a cosmetic composition which comprises a cosmetically acceptable vehicle, diluent or carrier.

Preferably, the compositions according to the invention are formulated to protect sensitive material against ultraviolet radiation, in particular solar radiation, comprising an effective amount of at least one compound of formulae (1) or (2). In a preferred embodiment of the invention, such compositions are for the photoprotection of the skin and/or the hair.

The compounds of formula (1) or (2) are generally formulated into the compositions of the invention in proportions of from 0.1% to 20% by weight, preferably from 0.5% to 10% by weight, relative to the total weight of the composition.

The compositions according to the invention can, of course, contain one or more complementary hydrophilic or lipophilic sunscreens that are active in the UV-A and/or UV-B range (absorbers), other than the subject compounds. These complementary screening agents are advantageously selected, in particular, from among the cinnamic derivatives, salicylic derivatives, camphor derivatives, triazine derivatives, benzophenone derivatives, dibenzoylmethane derivatives, β,β-diphenylacrylate derivatives, p-aminobenzoic acid derivatives, and the screening polymers and screening silicones described in WO-93/04665. Other examples of organic screening agents are provided in EP-A-0,487,404.

The compositions according to the invention may also contain agents for the artificial tanning and/or browning of the skin (self-tanning agents) such as, for example, dihydroxyacetone (DHA).

The compositions according to the invention may also contain pigments or nanopigments (average size of the primary particles: generally ranging from 5 nm to 100 nm, preferably from 10 nm to 50 nm) of coated or uncoated metal oxides, for example nanopigments of titanium dioxide (amorphous or crystallized in rutile and/or anatase form), of iron oxide, of zinc oxide, of zirconium oxide or of cerium oxide, which are all UV-photoprotective agents that are per se well known to this art. Standard coating agents therefor, include, moreover, alumina and/or aluminum stearate. Such coated or uncoated metal oxide nanopigments are described, in particular, in EP-A-0,518,772 and EP-A-0,518,773.

The subject photoprotective compositions may also comprise typical additives and adjuvants in the cosmetics field, such as fatty substances, organic solvents, silicones, thickeners, softeners, complementary sunscreens, antifoaming agents, moisturizers, fragrances, preservatives, surfactants, fillers, sequestering agents, anionic, cationic, nonionic or amphoteric polymers, or mixtures thereof, propellants, basifying or acidifying agents, dyes, colorants, pigments or nanopigments, in particular those intended to ensure a complementary photoprotective effect by physically blocking ultraviolet radiation, or any other ingredient usually used in cosmetics, in particular for the formulation of sunscreen compositions.

Among the organic solvents, exemplary are the lower alcohols and polyols such as ethanol, isopropanol, propylene glycol, glycerol and sorbitol.

Exemplary fatty substances include an oil or a wax or mixtures thereof, fatty acids, fatty acid esters, fatty alcohols, petroleum jelly, paraffin, lanolin, hydrogenated lanolin or acetylated lanolin. The oils can be selected from among animal, plant, mineral or synthetic oils, and in particular hydrogenated palm oil, hydrogenated castor oil, liquid petroleum jelly, liquid paraffin, purcellin oil, volatile or nonvolatile silicone oils, and isoparaffins.

Naturally, one skilled in this art will take care to select the optional complementary compound(s) indicated above and/or the amounts thereof such that the advantageous properties intrinsically associated with the compounds of this invention are not, or are not substantially, adversely affected by the addition(s) envisaged.

The cosmetic compositions of the invention are well suited for protecting the human epidermis or the hair against the damaging effects of ultraviolet rays, whether as a sunscreen composition or as a makeup product.

The subject compositions are advantageously formulated as lotions, thickened lotions, gels, creams, milks, powders or as solid sticks and can, optionally, be packaged as an aerosol and be in the form of a foam or a spray.

When the cosmetic compositions according to the invention are more particularly intended for protecting the human epidermis against UV irradiation or as sunscreen compositions, they can be formulated as suspensions or dispersions in solvents or fatty substances, or as emulsions (in particular of O/W or W/O type, but preferably O/W type) such as a cream or a milk, a vesicle dispersion, or as ointments, gels, solid sticks or aerosol foams. The emulsions can also contain anionic, nonionic, cationic or amphoteric surfactants.

When the cosmetic compositions according to the invention are used to protect the hair, they may be in the form of a shampoo, a lotion, a gel or a rinse-out composition to be applied before or after shampooing, before or after dyeing or bleaching, before, during or after permanent-waving or straightening of the hair, a styling or treating lotion or gel, a blow-drying or hair-setting lotion or gel, a hair lacquer or a composition for permanent-waving, straightening, dyeing or bleaching the hair.

When the cosmetic compositions according to the invention are formulated as makeup products for the eyelashes, the eyebrows, the skin or the hair, such as skin treatment creams, foundations, lipsticks, eyeshadows, blushers, eyeliners, mascara or coloring gels, same may be in anhydrous or aqueous, solid or pasty form, for example oil-in-water or water-in-oil emulsions, suspensions or, alternatively, gels.

This invention also features the subject compounds formulated into compositions well suited for photoprotecting sensitive material against ultraviolet radiation, in particular solar radiation.

This invention also features formulating a compound of formulae (1) or (2) into medicinal products for combatting the harmful effects of UV radiation.

The present invention also features use of a compound of formula (1) or (2) as an agent for screening out UV radiation, in particular for controlling the color of the skin.

Lastly, the present invention also features a non-therapeutic process for protecting the skin and/or the hair against the deleterious effects as ultraviolet radiation, in particular solar radiation, comprising applying to the skin or the hair an effective sunscreen amount of the cosmetic composition defined above, or of a compound of formula (1) or (2).

Too, this invention features a non-therapeutic process for controlling the variation in skin color due to UV radiation, which includes applying to the skin an effective amount of the cosmetic composition defined above, or of a compound of formula (1) or (2).

In order to further illustrate the present invention and the advantages thereof, the following specific examples are given, it being understood that same are intended only as illustrative and in nowise limitative.

EXAMPLE 1

Preparation of 4-methoxy-N-[3-[1,3,3,3-tetramethyl-1-[(trimethylsilyl)oxy]disiloxanyl]propyl] cinnamamide according to route C

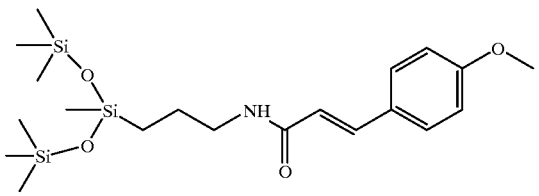

To a mixture of 3-[1,3,3,3-tetramethyl-1-[(trimethylsilyl)oxy]disiloxanyl]propylamine (27.96 g, 0.1 mol) and triethylamine (7.08 g, 0.07 mol) in 20 ml of dichloromethane was added dropwise para-methoxycinnamyl chloride (9.68 g, 0.05 mol) over 30 minutes. The temperature increased to 35° C. The mixture was refluxed for 3 hours. The reaction mixture was poured into 40 ml of water and extracted with dichloromethane. The organic phases were washed with water, dried over sodium sulfate and the solvent was then evaporated off. After purification by passage through a column of silica (eluent: 70/30 heptane/ethyl acetate), 19.9 g (yield: 93%) of the compound having the following characteristics were obtained:

(i) white powder
(ii) m.p.: 80–81° C.
(iii) UV (ethanol) $\lambda_{max}$=307 nm, $\epsilon_{max}$=24,825

Elemental analysis for $C_{20} H_{37} N O_4 Si_3$ theory: C: 54.62 H: 8.48 N: 3.18 found: C: 54.50 H: 8.45 N: 3.10

EXAMPLE 2

Preparation of di[2-methyl-3-[1,3,3,3-tetramethyl-1-[(trimethylsilyl)oxy]-disiloxanyl]propyl]4-methoxybenzalmalonate According to Route B

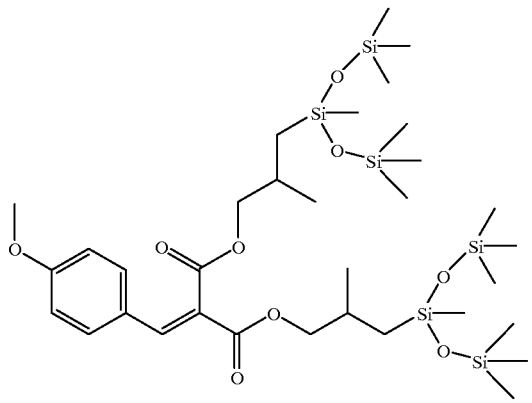

(a) First Step: Preparation of Di[2-methyl-3-[1,3,3,3-tetramethyl-1-[(trimethylsilyl)-oxy]disiloxanyl]propyl] malonate A solution of dimethallyl malonate (10 g, 0.047 mol) and catalyst (complex containing 3–3.5% by weight of Pt in cyclovinylmethylsiloxane, marketed by Hüls under the trademark Petrarch PC085: 200 μl) in 30 ml of toluene was heated to 80° C. 23 g (0.104 mol) of heptamethyltrisiloxane were added dropwise thereto over 20 minutes. The mixture was heated at 80° C. for 16 hours. The solvent and the excess heptamethyltrisiloxane were evaporated off under vacuum. The di[2-methyl-3-[1,3,3,3-tetramethyl-1-[(tri-methylsilyl)oxy]disiloxanyl]propyl] malonate was thus obtained in the form of an oil, which was employed as is in the next step.

(b) Second Step: Preparation of Di[2-methyl-3-[1,3,3,3-tetramethyl-1-[(trimethylsilyl)oxy]-disiloxanyl]propyl]4-methoxybenzalmalonate A mixture of the above compound (a) (10 g, 0.0234 mol) and anisaldehyde (2.72 g, 0.02 mol) in 20 ml of toluene was refluxed for 12 hours in the presence of 0.2 ml of piperidine and 0.12 ml of acetic acid. The reaction mixture was concentrated and chromatographed on silica (eluent: 50/50 heptane/$CH_2Cl_2$) in order to obtain 4.6 g of the target compound of Example 2 (yield: 30%) in the form of a colorless oil, characterized by its NMR and mass spectra:

(i) Mass spectrum: m/z=775.3 $(MH)^+$
(ii) Proton NMR: presence of an impurity (4%) of [2-methyl-3-[1,3,3,3-tetramethyl-1-[(tri-methylsilyl)oxy]disiloxanyl]propyl] 4-methoxycinnamate: m/z=455.2 $(MH)^+$
(iii) UV (ethanol) $\lambda_{max}$=310 nm, $\epsilon_{max}$=21,040

EXAMPLE 3

Preparation of Methyl 3-(4-methoxyphenyl)-2-(3-[1,3,3,3-tetramethyl-1-[(trimethylsilyl)oxy]-disiloxanyl]propylcarbamoyl)acrylate

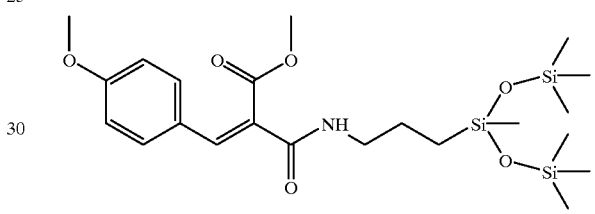

(a) First Step: Preparation of Methyl N-[3-[1,3,3,3-tetramethyl-1-[(trimethylsilyl)oxy]-disiloxanyl]propyl] malonamate To a mixture of 3-[1,3,3,3-tetramethyl-1-[(trimethylsilyl)oxy]disiloxanyl]propylamine (6.99 g, 0.025 mol) and triethylamine (20 g, 0.2 mol) in 20 ml of dichloromethane was added dropwise monomethyl malonyl chloride (3.4 g, 0.025 mol) over 30 minutes at 10° C. The reaction mixture was permitted to warm to room temperature and was refluxed for 2 hours. The reaction mixture was poured into 40 ml of water and extracted with dichloromethane. The organic phases were washed with water and dried over sodium sulfate and the solvent was then evaporated off. After purification by passage through a column of silica (eluent: 95/5 $CH_2Cl_2$/methanol), 2.2 g of a colorless oil were obtained, which product was employed as is in the following step.

(b) Second Step: Preparation of Methyl 3-(4-methoxyphenyl)-2-(3-[1,3,3,3-tetramethyl-1-[(tri-methylsilyl)oxy]disiloxanyl]-propylcarbamoyl)acrylate A mixture of the above compound (a) (1 g, 0.003 mol) and anisaldehyde (0.45 g, 0.0033 mol) in 1 ml of toluene was maintained at 80° C. for 12 hours in the presence of 0.03 g of piperidine and 0.018 g of acetic acid. The reaction mixture was concentrated and chromatographed on silica (eluent: 80/20 heptane/ethyl acetate) in order to obtain 1 g of the target compound of Example 3 in the form of a colorless oil, characterized by its NMR and mass spectra:

(i) Mass spectrum: m/z=498 $(MH)^+$
(ii) UV (ethanol) $\lambda_{max}$=312 nm, $\epsilon_{max}$=21,470

EXAMPLE 4

One specific example of a sunscreen emulsion having the following composition is given below (the amounts are expressed in % by weight relative to the total weight of the composition):

| | |
|---|---|
| (a) 80/20 mixture of cetylstearyl alcohol and oxyethylenated cetylstearyl alcohol (33 EO) marketed under the trademark "Dehsconet 390" by Tensia, | 7% |
| (b) mixture of glyceryl mono- and distearate, marketed under the trademark "Cerasynth SD" by ISP, | 2% |
| (c) cetyl alcohol | 1.5% |
| (d) polydimethylsiloxane marketed under the trademark "DC200 Fluid" by Dow Corning, | 1.5% |
| (e) $C_{12}$–$C_{15}$ alkyl benzoate marketed under the trademark "Finsolv TN" by Finetex, | 15% |
| (f) compound of Example 2 | 5% |
| (g) glycerol | 20% |
| (h) preservatives | qs |
| (i) demineralized water | qs 100% |

This O/W sunscreen emulsion was formulated according to standard techniques for the preparation of emulsions, by dissolving the screening agent in the fatty phase containing the emulsifiers, heating this fatty phase to about 70–80° C. and adding, with vigorous stirring, the water heated to the same temperature. Stirring was continued for 10 to 15 minutes, the mixture was then permitted to cool with moderate stirring, and lastly, at about 40° C., the preservatives were added.

A sunscreen cream particularly effective against UV radiation was thus obtained.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A silicone-substituted cinnamamide, benzalmalonamide or benzalmalonate compound having one of the following structural formulae (1) or (2):

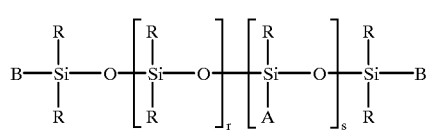

(1)

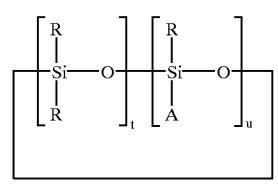

(2)

in which the radicals R, which may be identical or different, are each a saturated or unsaturated, linear or branched $C_1$–$C_{10}$ alkyl radical, a phenyl radical or a 3,3,3-trifluoropropyl radical, at least 80% by number of the radicals R being methyl radicals; the radicals B, which may be identical or different, are each a radical R or a radical A; r is an integer ranging from 0 to 3, inclusive; s is 0 or 1 and if s is 0, at least one of the two radicals B is A; u is equal to 1 or 2; t is an integer ranging from 2 to 5 inclusive; t+u is greater than or equal to 3; and A is a radical of formula (3) below:

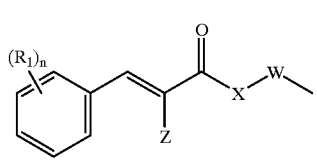

(3)

wherein $R_1$ is a linear or branched $C_1$–$C_{10}$ alkoxy radical, a linear or branched $C_1$–$C_{10}$ alkyl radical, a linear or branched $C_2$–$C_8$ alkenyl radical or a radical —$OSi(CH_3)_3$, with the proviso that two adjacent radicals $R_1$ may together form an alkylidenedioxy radical in which the alkylidene radical has from 1 to 2 carbon atoms, n is 0, 1, 2 or 3, Z is hydrogen, a $C_1$–$C_4$ alkyl radical, a radical —(C=O)$XR_2$ or a radical —(C=O)YW, X and Y, which may be identical or different, are each an oxygen atom or a radical —$NR_3$, W is a saturated or unsaturated, linear or branched $C_1$–$C_6$ alkanediyl radical, optionally substituted with a hydroxyl or saturated or unsaturated, linear or branched $C_2$–$C_8$ alkyl radical, $R_2$ is, independently, a $C_1$–$C_{12}$ alkyl radical, $R_3$ is, independently, hydrogen or a linear or branched $C_1$–$C_8$ alkyl radical, with the proviso that $R_2$ and $R_3$ may together form a heterocycle, with the added proviso that when Z=H, then X is the radical —$NR_3$—.

2. A silicone-substituted compound as defined by claim 1, wherein formulae (1) or (2), at least one of the following definitions exists:

R is methyl,

B is methyl, r is 0 or 1, s is 1, t+u ranges from 3 to 5, n is 0 or 1, $R_1$ is methoxy, $R_2$ is methyl or ethyl, and/or $R_3$ is H.

3. A silicone-substituted compound as defined by claim 1, wherein formulae (1) or (2), each of the following definitions exists:

R is methyl,

B is methyl, r=0, s=1, $R_1$ is methoxy.

4. A silicone-substituted compound as defined by claim 1, selected from among 4-methoxy-N-[3-[1,3,3,3-tetramethyl-1-[(trimethylsilyl)oxy]-disiloxanyl]propyl]cinnamamide; di-[2-methyl-3-[1,3,3,3,3-tetramethyl-1-[(trimethylsilyl)oxy]disiloxanyl]propyl]-4methoxybenzalmalonate; and methyl 3-(4-methoxyphenyl)-2-(3-[1,3,3,3-tetramethyl-1-[(trimethylxilyl)oxy]disiloxanyl]propylcarbamoyl)-acrylate.

5. A process for the preparation of a silicone-substituted compound as defined by claim 1, comprising hydrosilylating a compound of the following formula (6):

(6)

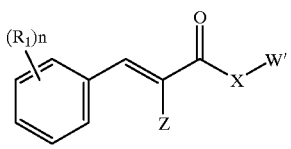

in which $R_1$, X, Z and $\underline{n}$ are defined as in formula (3) and in which W' is W, except having a double- or triple-bond endgroup, in the presence of a catalytically effective amount of a platinum catalyst, with an SiH compound having one of the following structural formulae (4) or (5):

(4)

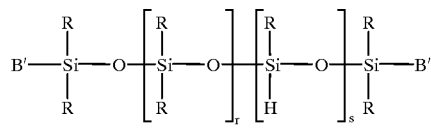

(5)

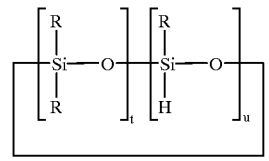

in which R, $\underline{r}$, $\underline{s}$, $\underline{t}$ and $\underline{u}$ are defined as in formulae (1) and (2); and the radicals B', which may be identical or different, are each a radical R or a hydrogen atom.

6. A process for the preparation of a silicone-substituted compound as defined by claim 1, comprising first reacting a compound having the structural formula (7):

(7)

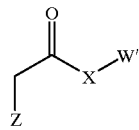

in which Z and X are as defined in formula (3) and W' is a saturated or unsaturated, linear or branched $C_1$–$C_6$ alkanediyl radical, optionally substituted with a hydroxyl or saturated or unsaturated, linear or branched $C_2$–$C_8$ alkyl radical, with the proviso that W' has a double- or triple-bond endgroup, with an SiH compound having one of the following structural formulae (4) or (5):

(4)

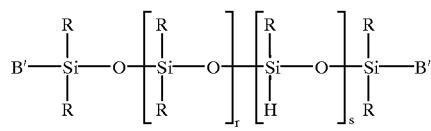

(5)

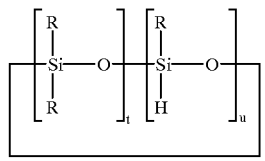

in which R, $\underline{r}$, $\underline{s}$, $\underline{t}$ and $\underline{u}$ are defined as in formulae (1) and (2); and the radicals B', which may be identical or different, are each a radical R or a hydrogen atom, and next reacting the compounds thus formed having the following structural formulae (7') and (7"):

(7')

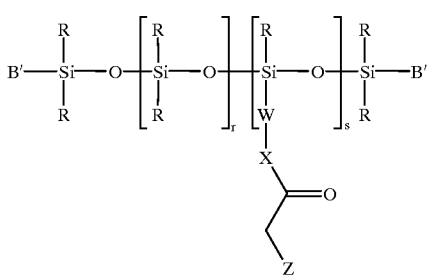

(7")

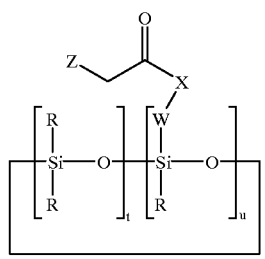

with a benzaldehyde of formula (8) below:

(8)

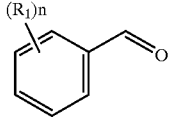

in which formulae (7), (7') and (8) X, W', Z, $R_1$ and $\underline{n}$ are as defined above.

7. A process for the preparation of a silicone-substituted compound as defined by claim 1, wherein formula (3) X is the —NH— radical, comprising reacting a compound having the structural formula (9):

(9)

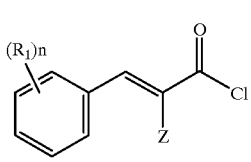

in which $R_1$, Z and $\underline{n}$ are as defined in formula (3), with an aminosiloxane, having one of the following structural formulae (10) or (11):

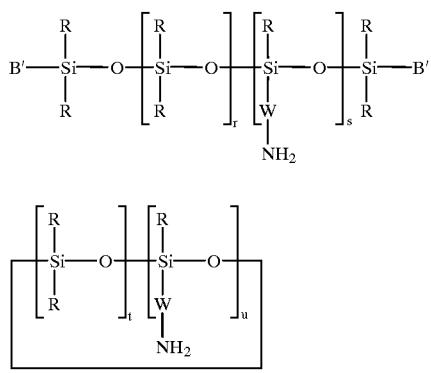

in which R, r, s, t and u are as defined in formulae (1) and (2), and the radicals B', which may be identical or different, are each a radical R or an —NH$_2$ radical.

8. A photoprotective cosmetic composition suited for photoprotecting the skin and/or hair against the deleterious effects of UV radiation, comprising an effective UV-screening amount of at least one silicone-substituted compound as defined by claim 1, formulated into a topically applicable cosmetically acceptable vehicle, diluent or carrier therefor.

9. The photoprotective cosmetic composition as defined by claim 8, comprising from 0.1% to 20% by weight of said at least one silicone-substituted compound.

10. The photoprotective composition as defined by claim 9, comprising from 0.5% to 10% by weight of said at least one silicone-substituted compound.

11. The photoprotective composition as defined by claim 8, formulated as a lotion, gel, cream, milk, emulsion, powder, solid stick, foam, spray, or ointment.

12. The photoprotective composition as defined by claim 8, formulated as a shampoo, hair dye, hair bleach, hair wave, hair lacquer, or hair straightener.

13. The photoprotective composition as defined by claim 8, further comprising at least one additional UV-A and/or UV-B sunscreen.

14. The photoprotective composition as defined by claim 8, further comprising at least one active agent for the artificial tanning and/or browning of human skin.

15. The photoprotective composition as defined by claim 8, further comprising a photoprotecting effective amount of at least one inorganic pigment or nanopigment.

16. The photoprotective composition as defined by claim 8, further comprising at least one fatty substance, solvent, silicone, thickener, softener, anti-foaming agent, moisturizer, fragrance, preservative, surfactant, filler, sequestering agent, polymer, basifying or acidifying agent, or colorant.

17. A UV-sensitive shaped article, containing an effective UV-photoprotecting amount of at least one silicone-substituted compound as defined by claim 1.

18. The shaped article as defined by claim 17, comprising a plastic.

19. A method for photoprotecting human skin and/or hair against the deleterious effects of UV irradiation, comprising topically applying thereto an effective UV-screening amount of the photoprotective composition as defined by claim 8.

20. A method for controlling variation in skin color promoted by UV irradiation, comprising topically applying thereto an effective UV-screening amount of the photoprotective composition as defined by claim 8.

* * * * *